United States Patent [19]

Stenberg et al.

[11] 4,374,088
[45] Feb. 15, 1983

[54] APPARATUS FOR THE TRANSFER OF ONE OR MORE SUBSTANCES BETWEEN A GAS AND A LIQUID

[75] Inventors: Kaj O. Stenberg, Staffanstorp; Lars J. C. Travén, Lund; Ingvar F. Losell, Staffanstorp; Bo A. Johnsson, Landskrona, all of Sweden

[73] Assignee: Gambro Heart-Lung Products AB, Sweden

[21] Appl. No.: 314,831

[22] PCT Filed: Apr. 3, 1980

[86] PCT No.: PCT/SE80/00096
§ 371 Date: Oct. 22, 1981
§ 102(e) Date: Oct. 22, 1981

[87] PCT Pub. No.: WO81/02836
PCT Pub. Date: Oct. 15, 1981

[51] Int. Cl.³ .............................................. A61M 1/03
[52] U.S. Cl. ........................................ 422/46; 422/45; 422/47; 261/DIG. 28
[58] Field of Search ................. 261/DIG. 28; 422/45, 422/46, 47

[56] References Cited

U.S. PATENT DOCUMENTS

| | | | |
|---|---|---|---|
| 3,536,305 | 10/1970 | Lefrancois | 261/93 |
| 3,790,141 | 2/1974 | Champeau | 261/77 |
| 4,033,724 | 7/1977 | Tamiya | 422/45 |
| 4,065,264 | 12/1977 | Lewin | 128/DIG. 3 |
| 4,067,696 | 1/1978 | Curtis | 261/DIG. 28 X |
| 4,182,739 | 1/1980 | Curtis | 422/47 |
| 4,231,988 | 11/1980 | Kurata | 422/47 |
| 4,254,081 | 3/1981 | Streczyn et al. | 422/46 |

FOREIGN PATENT DOCUMENTS

| | | |
|---|---|---|
| 2369 | 6/1979 | European Pat. Off. . |
| 3548 | 8/1979 | European Pat. Off. . |
| 7489 | 2/1980 | European Pat. Off. . |
| 1065140 | 3/1960 | Fed. Rep. of Germany . |
| 1071291 | 6/1960 | Fed. Rep. of Germany . |
| 2114340 | 10/1972 | Fed. Rep. of Germany . |
| 2834701 | 3/1979 | Fed. Rep. of Germany . |
| 1312112 | 11/1962 | France . |
| 1546223 | 10/1968 | France . |
| 2421669 | 11/1979 | France . |
| 554191 | 9/1974 | Switzerland . |
| 715612 | 9/1954 | United Kingdom . |
| 1220924 | 1/1971 | United Kingdom . |
| 1554772 | 10/1979 | United Kingdom . |

*Primary Examiner*—Arthur D. Kellogg
*Attorney, Agent, or Firm*—Lerner, David, Littenberg & Samuel

[57] ABSTRACT

A device for the transfer of one or more substances between a gas and a liquid, the gas being introduced into the liquid in the form of bubbles from which the said substances are transferred to the liquid whereupon the excess gas is removed together with any substances transferred from the liquid to the gas. Characteristic for the device is a narrow annular gap (10), arranged vertically, for the liquid, a gas inlet (20), arranged in close connection to this gap (10), this gas inlet being adapted so that it introduces the gas uniformly distributed along the whole periphery of the gap (10), and means (34,36) for the removal of the excess gas.

The device is intended in particular to be used as a so-called oxygenator when the said liquid is blood and the said gas is oxygen or an oxygen mixture. Carbon dioxide from the blood will then be removed together with the excess gas.

27 Claims, 2 Drawing Figures

APPARATUS FOR THE TRANSFER OF ONE OR MORE SUBSTANCES BETWEEN A GAS AND A LIQUID

TECHNICAL FIELD

The present invention relates to a device for the transfer of one or more substances between a gas and a liquid, the gas being introduced into the liquid in the form of bubbles from which the said substances are transferred to the liquid, whereupon the excess gas is removed together with any substances transferred from the liquid to the gas.

In the first place the device in accordance with the invention is intended to be used for the oxygenation of blood, i.e. as an oxygenator. However, it will be clear to those versed in the art that the construction in accordance with the invention can also be used for many other purposes, that is to say, whenever substances from a gas are to be made to react with or to be dissolved in a liquid or else when substances are to be exchanged between gases and liquids.

BACKGROUND ART

Insofar as oxygenators are concerned, three main types can be distinguished. The oldest of these is probably the type where a film of blood is formed in direct contact with an oxygen-containing atmosphere. In a second type the oxygen instead is made to diffuse through a semipermeable membrane from an oxygen-containing atmosphere on the one side of the membrane to the blood on the other side. The third type, to which the device in accordance with the present invention belongs, is known as a bubble oxygenator. In this type of device, gas bubbles containing oxygen are sprayed directly into the blood so as to act directly upon the same. After the desired action, the excess gas is removed. Examples of constructions of the lastmentioned type, that is to say, of bubble oxygenators, are shown inter alia, in the following U.S. Pat. Nos: 3,175,555; 2,934,067; 3,545,937; 4,037,622; 3,468,831; 3,488,158; 3,615,238; 4,058,369; 3,578,411; 3,291,568; 4,033,724; 3,827,860; 3,853,479; 4,067,696; 4,065,264; 4,138,464; 4,138,288.

SUMMARY OF THE INVENTION

The device in accordance with the invention is characterized by a narrow annular gap arranged vertically for the liquid, by a gas inlet arranged in close connection to this gap, this gas inlet being adapted so that it introduces and distributes the gas uniformly along the whole periphery of the gap, and by means for the removal of excess gas. In this manner a very effective mixture of gas and liquid is obtained. In addition, there are other advantages, which will be evident from the following.

The gas inlet is constituted preferably of a series of holes arranged along the periphery of the upper end of the gap where this gap changes into a widened, annular, vertical cylindrical space. As a result, there is no need for a sudden increase in the rate of flow.

The abovementioned gap and the adjoining annular cylinder space are formed appropriately between an intermediate vessel open at the top and a combined gas and liquid inlet pipe inserted therein. This design is appropriate for easy assembly. At the same time it permits a suitable design of the path of the liquid flow. The inlet pipe may comprise a central liquid inlet duct, into which the liquid is introduced at its upper end and which in the lower part smoothly changes into the said gap.

The annular cylindrical space, appropriately includes a heat exchanger for the tempering, i.e., heating and/or cooling, of the gas and liquid mixture obtained. This heat exchanger may consist, for example, of an annular cylinder preferably with longitudinal heat transfer ribs on the inside as well as on the outside, the outer ribs being arranged so that they adjoin relatively tightly the inner wall and outer wall respectively of the annular cylinder space, so that this is divided into separate longitudinal ducts. In this way a uniform distribution of the gas as well as of the liquid is achieved in the whole annular cylindrical space outside the actual heat exchanger.

The annular cylindrical space appropriately terminates at its upper end in an annular throttling gap, which also contributes to a uniform distribution of the gas as well as of the liquid. This throttling gap can be in the form of a spillway between the top edge of the intermediate vessel and a lid arranged above the same. In this manner a simple design from the point of view of assembly is achieved, in particular if the lid is made integral with the combined gas and liquid input pipe.

The said means for the removal of excess gas may comprise a filter separated from the outer surface of the intermediate vessel by a gap. This filter may consist, for example, of a foam of polyurethane or other suitable material surrounded by a filter mantle and coated with an antifoaming agent.

The intermediate vessel with the gas and liquid inlet pipe arranged therein and the filter arranged outside the same are appropriately enclosed in an outer casing comprising a bottom outlet for the liquid and a gas outlet located at a higher elevation for the excess gas. The lower portion of the bottom of this outer casing may be in the form of an annular gap comprising a base which slopes evenly towards the bottom outlet. In this way an even movement of the liquid is obtained without any stagnation points in the same.

The combined gas and liquid inlet pipe can be connected at its inlet end to a branch pipe which can freely rotate in relation to the pipe and which has one or more inlets arranged at an angle in respect of the longitudinal direction of the pipe. Such a construction is particularly appropriate when the device is used as an oxygenator. The direction towards the patient will be of no importance from the point of view of operation of the device, that is to say, independent of the angular position of the connecting nipples in relation to the annular gap.

The combined gas and liquid inlet pipe is appropriately provided with a sterile filter at the gas inlet.

As mentioned previously, the construction in accordance with the invention is used preferably as a so-called oxygenator in which the said liquid is blood and the said gas is oxygen or an oxygen mixture, from which oxygen is transferred to the blood and to which carbon dioxide is transferred from the blood. The invention is described therefore in the following with reference to such a construction made up of a number of vessels arranged concentrically inside one another which can easily be sealed off in relation to one another.

DETAILED DESCRIPTION OF THE PREFERRED EMBODIMENT

Figure 1:
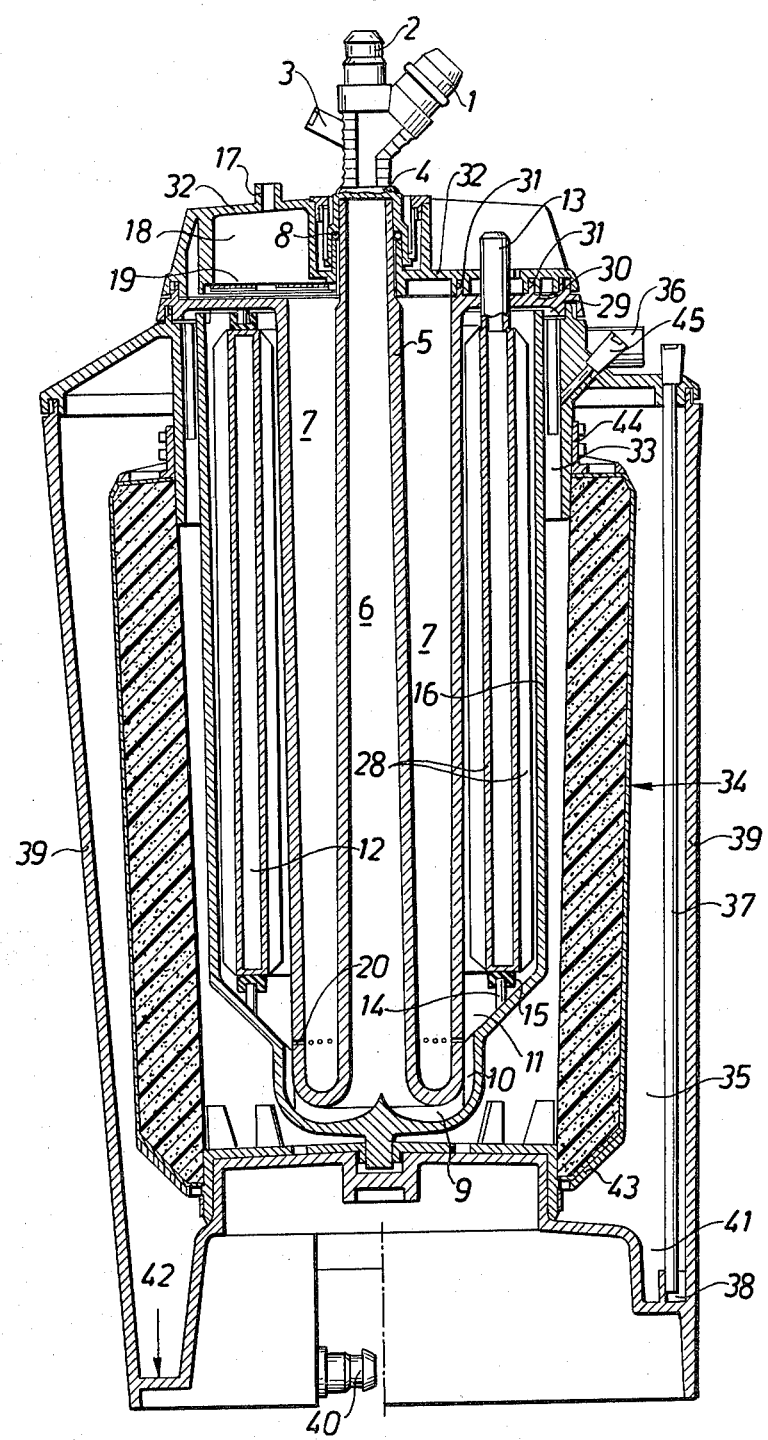
FIG. 1 shows a longitudinal section through an oxygenator in accordance with the invention.

In the embodiment of the subject of the invention shown as an example, venous blood from a patient is fed to the inlet nipple 1 arranged at the top. This nipple is arranged jointly with another inlet nipple 2 and a sampling nipple 3 on a branch pipe 4 which otherwise is freely rotatable in relation to the oxygenator. This branch pipe 4 is threaded onto a combined liquid-gas conduit which in the preferred embodiment comprises a double-walled inlet pipe 5 arranged centrally in the oxygenator. The pipe 5 comprises an inner, central liquid inlet duct 6 and an outer annular gap or chamber 7 for gas supply. Between the inlet pipe 5 and the branch pipe 4 there is a packing 8. The blood is thus adapted to flow vertically down through the duct 6 and via a smooth transition 9 into a narrow annular gap 10. This gap 10 subsequently changes into a widened annular vertical cylindrical space 11 which contains a heat exchanger 12. This heat exchanger 12 is provided with a liquid inlet 13 for a heat exchange fluid and a liquid outlet, not shown. The heat exchanger 12 is arranged on pins 14 with shock absorbers 15 of silicone rubber or the like.

The gap 10 and the widened vertical cylinder space 11 arranged above it are formed between the centrally arranged liquid inlet pipe 5 and an intermediate vessel 16 which is open at the top.

Thus, it will be appreciated, using the narrow annular gap 10 as a reference point, that the flow path for the liquid or blood includes an upstream portion comprising the liquid inlet duct 6, a downstream portion comprising the annular vertical cylindrical space 11 and an intermediate portion for directing the blood from the upstream portion to the downstream portion. In the preferred embodiment, the intermediate portion comprises the smooth transition 9 and the narrow annular gap 10. It should also be noted that the intermediate portion has a cross sectional dimension which is no greater than the cross sectional dimension of the upstream and downstream portions, i.e., the flow area of the intermediate portion is no greater than the flow area of the upstream and downstream portions. Also, it will be appreciated that the cross sectional dimension or flow area through the narrow annular gap 10 is less than the cross sectional dimension or flow area of the upstream and downstream portions.

Figure 2:
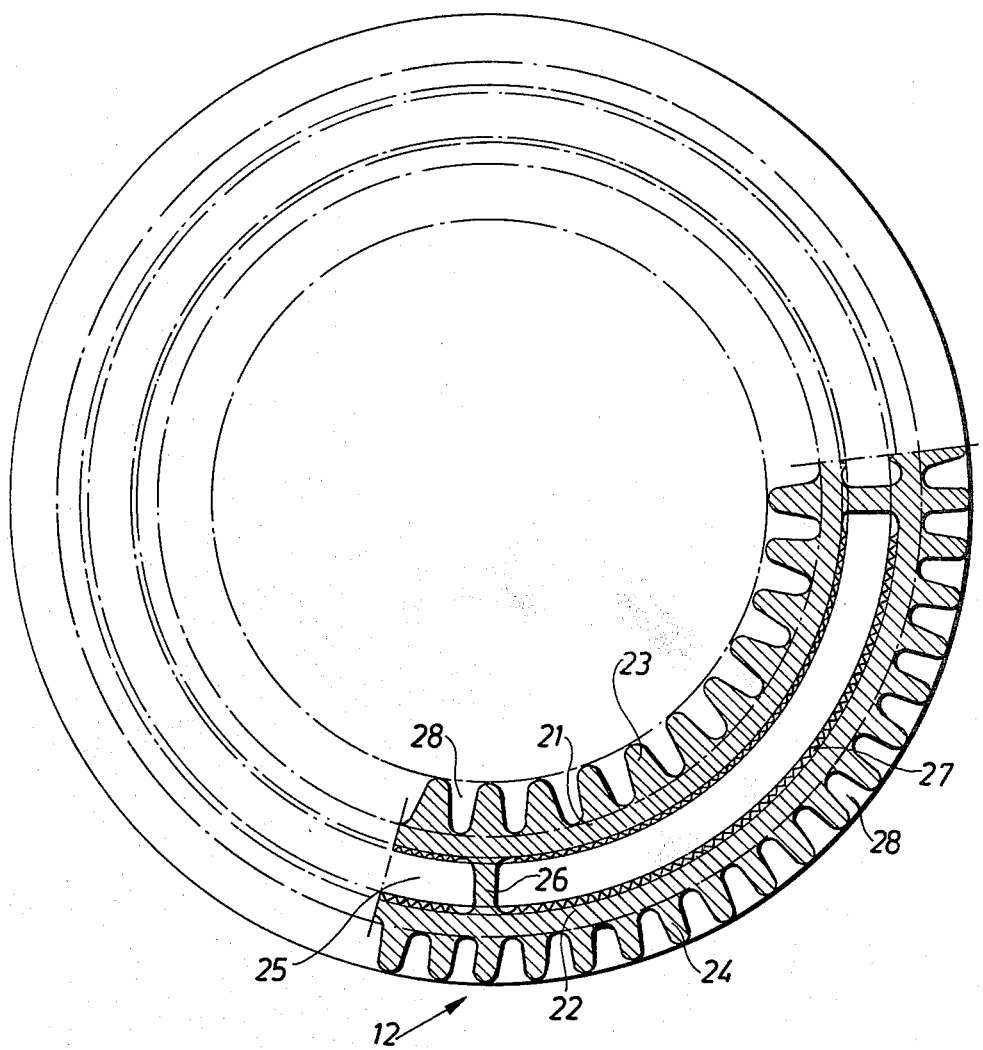
FIG. 2 shows a transverse section through a heat exchanger incorporated in the oxygenator in accordance with the invention.

The gas, which consists of oxygen or an oxygen mixture when the device is used as an oxygenator, is fed via a connecting nipple 17, an inlet chamber 18 and a sterile filter 19 into the annular space 7 in the inlet pipe 5. Through a series of holes 20, which are evenly distributed along the periphery of the gap 10 at its upper end, the gas is directed into the blood just where the gap 10 changes into the widened cylinder space 11. As a result a very effective mixture of blood and gas is achieved. This mixture is further improved by the subsequent heat exchanger 12 which is shown in transverse section in FIG. 2. This heat exchanger consists in the example shown of an annular cylinder with an inner wall 21 and an outer wall 22, which are provided with inner longitudinal ribs 23 and outer longitudinal ribs 24 respectively. Between the inner and outer walls vertical ducts 25 are formed, separated by partitions 26 for the conduction of a heat exchanger fluid. Moreover, smaller vertical ribs 27 which enlarge the surface are arranged on the inner walls of the vertical ducts 25. The heat exchanger is an dimensioned that in assembled condition the inner ribs 23 and the outer ribs 24 will be situated close to the outer wall of the inlet pipe 5 and the inner wall of the intermediate vessel 16 respectively.

Thus a mixture of gas and liquid flows vertically upwards in the vertical ducts 28 formed by the ribs 23 and 24. At the upper end of the heat exchanger the gas and liquid mixture flows through an annular throttling gap 29. This gap is in the form of a spillway between the upper edge of the intermediate vessel 16 and a lid 30 arranged above the same. This lid 30 is made integral with the double-walled inlet pipe 5 and is in turn connected via seals 31 to an outer lid 32 comprising, among other things, the gas inlet chamber 18 and the sterile filter 19.

From the throttling gap in the form of a spillway 29 the gas mixture flows downwardly through a gap 33 between the intermediate vessel 16 and a filter 34. The blood then flows out through the filter 34 into a blood collecting space 35, whilst the excess gas instead flows out through an outlet 36. The gap 33 and the blood collecting space 35 thus comprise an outlet portion of the flow path for the blood.

The sampling nipple 3 is intended for the sampling of venous blood. With the help of a pipe 37, which terminates in a sampling compartment 38, samples of arterial blood can also be taken.

The intermediate vessel 16 with the inlet pipe 5 arranged therein and the filter 34 arranged outside the same are enclosed in an outer casing 39 with a bottom outlet 40 for the separated liquid phase and which also contains the gas outlet 36, discussed above, for excess gas. The lower part of the bottom of this outer casing is in the shape of an annular gap 41 with a base 42 sloping evenly towards the bottom outlet 40.

The construction as a whole can be said to be composed of a number of vessels inserted into one another. The outermost is the outer casing 39. Inserted into this is a "vessel" formed of the filter 34 which at the bottom is limited by a bottom ring 43 and at the top by a fastening ring 44. With the help of the ring 44 the filter is fixed on the outside of the vessel 16 described above as the intermediate vessel. Into the latter is then inserted the inlet pipe 5 which is in the form of a double-walled vessel.

Finally, an inlet nipple 45 is intended for the feed of medicine, heparin or other additives to the mixture of gas and blood before these pass the filter 34.

With regard to the holes 20, it may be mentioned that in a preferred embodiment they number approximately one hundred and have a diameter of approx. 0.2–0.4 mm. In this preferred embodiment the width of the gap 10 is approx. 3.25 mm, which ensures a good mixture at normal blood flows which are between two and six liters per minute.

Naturally, the invention is not limited to the embodiment described above, but can be varied within the scope of the following claims. The individual shape of the different components, for example, may be varied within wide limits.

We claim:

1. Apparatus for the transfer of one or more substances between a gas and a liquid, said apparatus comprising:

liquid conduction means defining a flow path for a liquid, said liquid conduction means including means defining a vertically arranged, narrow annular gap in said flow path, said annular gap having a dimension thereacross which is less than the dimension across said flow path upstream and downstream of said narrow annular gap;

gas introduction means for introducing a gas in the form of bubbles into said liquid as said liquid is conducted along said flow path to thereby effect transfer of substances between said gas and said liquid, said gas introduction means being arranged about the periphery of said narrow annular gap so as to uniformly introduce gas bubbles along the entire periphery of said annular gap into said liquid as said liquid is conducted through said narrow annular gap; and removal means along said flow path downstream of said narrow annular gap for removing excess gas from said liquid together with any substances transferred from said liquid to said gas.

2. The device of claim 1 wherein said flow path includes an upstream portion, a downstream portion and an intermediate portion for effecting a change in direction of flow of said liquid between said upstream and downstream portions, said intermediate portion having an inlet and communicating with said upstream portion and an outlet end communicating with said downstream portion, said downstream portion being at a higher elevation than said outlet end of said intermediate portion, and wherein said narrow annular gap comprises a part of said intermediate portion and is located adjacent said outlet end of said intermediate portion whereby said gas bubbles introduced by said gas introduction means into said liquid are directed upwardly with said liquid into said downstream portion of said flow path.

3. The apparatus of claim 1 wherein said intermediate portion has a dimension thereacross which is no greater than the dimension across said upstream and said downstream portions.

4. The apparatus of claim 1 wherein said annular gap includes an outlet for directing said liquid into said flow path downstream of said annular gap, and wherein said gas introduction means is arranged adjacent said outlet of said annular gap so as to uniformly introduce gas bubbles along the entire periphery of said annular gap into said liquid as said liquid is conducted through said outlet of said annular gap.

5. The apparatus of claim 2 wherein said downstream portion adjacent said outlet end of said intermediate portion comprises an annular space having a lateral dimension which is greater than the dimension across said narrow annular gap, and wherein said gas introduction means comprises a series of flow openings arranged along the periphery of said annular gap adjacent said outlet end of said intermediate portion.

6. The apparatus of claim 2 wherein said liquid conduction means comprises a substantially cylindrical hollow vessel having a closed surface at the lower end thereof, and a combined liquid-gas conduit means having a substantially cylindrical outer surface and being concentrically disposed within said hollow vessel, said combined liquid-gas conduit means defining said upstream portion, and said combined liquid-gas conduit means and said hollow vessel being shaped to together define said intermediate portion and said downstream portion of said flow path between said conduit means and said hollow vessel, the lower portion of said hollow vessel and the lower portion of said combined liquid-gas conduit means together defining said intermediate portion of said flow path with said narrow annular gap comprising a first annular cylindrical space between said combined liquid-gas conduit means and said hollow vessel, and said downstream portion comprising a second annular cylindrical space between said combined liquid-gas conduit means and said hollow vessel which is at a higher elevation than said first annular cylindrical space.

7. The apparatus of claim 6 wherein said liquid-gas conduit means comprises a central liquid duct and an annular gas supply chamber, said annular gas supply chamber surrounding said liquid duct and said liquid duct being open at its lower end so as to communicate with said inlet end of said intermediate portion of said flow path.

8. The apparatus of claim 7 wherein said liquid-gas conduit means includes a first wall section having a circular cross sectional shape to define said liquid duct therewithin, a second longitudinally extending wall section having a circular cross section, said second wall section being spaced from and concentrically arranged with respect to said first wall section to define said annular gas supply chamber between said first and second wall sections, said first and second wall sections being joined at the lower ends thereof by a substantially closed intermediate wall section, said intermediate wall section being spaced from the lower end of said hollow vessel to define said inlet end of said intermediate portion of said flow path.

9. The apparatus of claim 8 wherein said liquid duct is parallel to said downstream portion such that said liquid is conducted downwardly through said liquid duct and is conducted upwardly through said downstream portion, and wherein said intermediate portion smoothly changes the direction of flow of said liquid from said liquid duct into said downstream portion.

10. The apparatus of claim 9 wherein said annular gap is defined between a part of said second wall section and a part of said hollow vessel, and wherein said liquid is conducted upwardly through said annular gap.

11. The apparatus of claim 10 wherein said gas introduction means comprises a series of openings through said second wall section at an elevation adjacent the upper end of said narrow annular gap, said series of openings being arranged about said second wall section so as to uniformly introduce gas bubbles into said annular gap.

12. The apparatus of claim 6 further including heat exchanger means for tempering the gas-liquid mixture being conducted through said downstream portion, said heat exchanger means being positioned in said downstream portion of said flow path.

13. The apparatus of claim 12 wherein said heat exchanger means comprises an annular cylindrical heat exchange member having an inner cylindrical heat exchange surface and an outer cylindrical heat exchange surface defining a least one longitudinally extending duct between said inner and outer heat exchange surfaces.

14. The apparatus of claim 13 wherein said inner and outer heat exchange surfaces each have a plurality of longitudinally extending rib members therealong, said rib members on said inner surface being in close proximity to said cylindrical outer surface of said combined liquid-gas conduit means, and said rim member of said outer heat exchange surface being in close proximity to the inner wall of such hollow vessel.

15. The apparatus of claim 14 wherein said at least one longitudinally extending duct of said heat exchange member includes a plurality of rib members therealong.

16. The apparatus of claim 13 further including an outer vessel spaced from and surrounding said hollow vessel, the annular space between said hollow vessel and said outer vessel defining an outlet portion of said flow path downstream of said downstream portion.

17. The apparatus of claim 16 further including cover means overlying the upper end of said hollow vessel, said cover means being spaced from the upper edge of said hollow vessel to define an annular throttling gap for directing the liquid-gas mixture therethrough into said outlet portion after passing through said downstream portion.

18. The apparatus of claim 17 wherein removal means comprises means supported in said annular space between said hollow vessel and said outer vessel for filtering excess gas from said liquid-gas mixture and passing liquid therethrough.

19. The apparatus of claim 18 further including liquid outlet means arranged in the lower end of said outer vessel for liquid which has passed through said filter means, and wherein said removal means further includes gas outlet means arranged at an elevation above said liquid outlet means for directing excess gas from said apparatus, said gas outlet means communicating with said outlet portion of said flow path upstream of said filtering means.

20. The apparatus of claim 19 wherein said outer vessel includes means defining an annular passageway in the lower end thereof for directing liquid received therein after passing through said filter means towards said liquid outlet means.

21. The apparatus of claim 7 further including liquid inlet connection means connected to said liquid duct, said liquid inlet connection means being rotatably mounted with respect to said liquid duct and including a plurality of liquid inlets for introducing liquid into said liquid duct.

22. The apparatus of claim 21 further including gas filter means for filtering said gas before said gas is introduced into said annular gas supply chamber.

23. The apparatus of claim 17 wherein said outer vessel has a closed surface at the lower end thereof and an open upper end; wherein said hollow vessel has an open upper end and is adapted to be inserted into said outer vessel through said open upper end of said outer vessel; wherein said combined liquid-gas conduit means is adapted to be inserted into said hollow vessel through the open upper end thereof; and further including means for sealing said outer vessel, said hollow vessel and said combined liquid-gas conduit means from one another so as to define said flow path.

24. The apparatus of any one of claims 1–23 wherein said liquid comprises blood said wherein said gas comprises a gas containing oxygen.

25. Apparatus for the transfer of one or more substances between a gas and a liquid, said apparatus comprising:
liquid conduction means defining a flow path for a liquid, said flow path including an upstream portion, a downstream portion, and an intermediate portion for effecting a change in direction of flow of said liquid between said upstream and downstream portions, said upstream portion being substantially parallel to said downstream portion so that said liquid is conducted along said upstream portion into said intermediate portion and so that said liquid is conducted from said intermediate portion into said downstream portion, said intermediate portion having a dimension thereacross which is no greater than the dimension across said upstream and downstream portions, and said intermediate portion further including means defining a narrow annular gap having a dimension thereacross which is less than the dimension across said upstream and downstream portions of said flow path;
gas introduction means for introducing a gas in the form of bubbles into said liquid as said liquid is conducted along said flow path to thereby effect transfer of substances between said gas and said liquid, said gas introduction means being arranged about the periphery of said narrow annular gap so as to uniformly introduce gap bubbles along the entire periphery of said annular gap into said liquid as said liquid is conducted through said narrow annular gap; and
removal means along said flow path downstream of said narrow annular gap for removing excess gas from said liquid together with any substances transferred from said liquid to said gas.

26. The apparatus of claim 25 wherein said upstream and said downstream portions are arranged vertically, and wherein said narrow annular gap is arranged vertically at a lower elevation than said downstream portion.

27. Apparatus for the transfer of one or more substances between a gas and a liquid, said apparatus comprising:
liquid conduction means defining a flow path for a liquid, said liquid conduction means including means defining a vertically arranged, narrow annular gap in said flow path, said annular gap having a dimension thereacross which is less than the dimension across said flow path upstream and downstream of said narrow annular gap, and said narrow annular gap including an outlet for directing said liquid into said flow path downstream of said annular gap;
gas introduction means for introducing a gas in the form of bubbles into said liquid as said liquid is conducted along said flow path to effect transfer of substances between said liquid and said gas, said gas introduction means being arranged about the periphery of said narrow annular gap and adjacent said outlet of said annular gap so as to uniformly introduce gas bubbles along the entire periphery of said annular gap into said liquid as said liquid is conducted through said outlet of said annular gap into said downstream portion; and
removal means along said flow path downstream of said narrow annular gap for removing excess gas from said liquid together with any substances transferred from said liquid to said gas.

* * * * *